(12) United States Patent
Wang et al.

(10) Patent No.: US 9,539,271 B2
(45) Date of Patent: Jan. 10, 2017

(54) APPLICATION OF DEPOLYMERIZED HOLOTHURIAN GLYCOSAMINOGLYCANS (DHG) IN PREPARATION OF DRUG FOR PREVENTION AND TREATMENT OF THROMBOEMBOLIC DISEASES

(71) Applicants: Shanghai Kairun Biology Medicine Limited Liability Company, Shanghai (CN); Harbin Hongdoushan Bio-Pharm Co., Ltd., Shangzhi (CN); Heilongjiang Hongdoushan Pharmaceutical Co., Ltd., Harbin, Heilongjiang (CN)

(72) Inventors: Zhiguo Wang, Shangzhi (CN); Quanhai Liu, Shanghai (CN); Xuehai Wu, Shanghai (CN)

(73) Assignees: Shanghai Kairun Biology Medicine Limited Liability Company (CN); Harbin Hongdoushan Bio-Pharm Co., Ltd. (CN); Heilongjiang Hongdoushan Pharmaceutical Co., Ltd. (CN)

( * ) Notice: Subject to any disclaimer, the term of this patent is extended or adjusted under 35 U.S.C. 154(b) by 137 days.

(21) Appl. No.: 14/383,376

(22) PCT Filed: Mar. 1, 2013

(86) PCT No.: PCT/CN2013/000217
§ 371 (c)(1),
(2) Date: Sep. 5, 2014

(87) PCT Pub. No.: WO2013/131406
PCT Pub. Date: Sep. 12, 2013

(65) Prior Publication Data
US 2015/0051165 A1 Feb. 19, 2015

(30) Foreign Application Priority Data

Mar. 5, 2012 (CN) .......................... 2012 1 0055824
Aug. 24, 2012 (CN) .......................... 2012 1 0306680

(51) Int. Cl.
| | | |
|---|---|---|
| A61K 31/726 | (2006.01) | |
| C08B 37/00 | (2006.01) | |
| A61K 31/7028 | (2006.01) | |
| A61K 35/616 | (2015.01) | |
| A61K 9/00 | (2006.01) | |
| A61K 9/19 | (2006.01) | |

(52) U.S. Cl.
CPC ......... *A61K 31/7028* (2013.01); *A61K 9/0019* (2013.01); *A61K 31/726* (2013.01); *A61K 35/616* (2013.01); *C08B 37/0063* (2013.01); *C08B 37/0066* (2013.01); *C08B 37/0069* (2013.01); *A61K 9/19* (2013.01)

(58) Field of Classification Search
None
See application file for complete search history.

(56) References Cited

FOREIGN PATENT DOCUMENTS

| CN | 1579415 | * | 2/2005 | ........... A61K 31/726 |
|---|---|---|---|---|
| CN | 1858067 | A | 11/2006 | |
| CN | 101451157 | A | 6/2009 | |
| CN | 101624426 | * | 1/2010 | ............. C08B 37/00 |
| CN | 101624426 | A | 1/2010 | |
| CN | 101890041 | A | 11/2010 | |

OTHER PUBLICATIONS

Imanari et al., "Oral Absorption and Clearance of Partially Depolymerized Fucosyl Chondroitin Sulfate from Sea Cucumber" Thrombosis Research (1999) vol. 93 pp. 129-135.*
Wu et al., "Physicochemical characteristics and anticoagulant activities of low molecular weight fractions by free-radical depolymerization of a fucosylated chondroitin sulphate from sea cucumber *Thelenata ananas*" Food Chemistry (2010) vol. 122 pp. 716-723.*
Myron et al., "Fucosylated chondroitin sulfate diversity in sea cucumbers: A review" Carbohydrate Polymers (2014) vol. 112, pp. 173-178.*
International Search Report for Application No. PCT/CN2013/000217 dated Jun. 6, 2013.

(Continued)

*Primary Examiner* — Eric Olson
(74) *Attorney, Agent, or Firm* — Lerner, David, Littenberg, Krumholz & Mentlik, LLP

(57) ABSTRACT

The present invention discloses an application of depolymerized holothurian glycosaminoglycans (DHG) in preparation of a drug for the prevention and treatment of thromboembolic diseases. The DHG is more than one type of DHG with weight-average molecular weights between 26,000 and 45,000 Da. When being intravenously or subcutaneously injected, the drug using the DHG with weight-average molecular weights between 26,000 and 45,000 Da as an active ingredient has a significant anticoagulant effect, while at the same time, has little side effects, and is effective for use in the prevention and treatment of the thromboembolic diseases. For an injection of DHG with weight-average molecular weights between 26,000 Da and 45,000 Da, the blood coagulation time is prolonged and the anticoagulant effect is enhanced as the dosage increases; the subcutaneous administration is used and is more favorable for use in the drug, and the convenience and safety of use the drug are improved.

19 Claims, 2 Drawing Sheets

(56) References Cited

OTHER PUBLICATIONS

Shen, Weizhang, et al., Antithrombotic mechanism of holothurian glycosaminoglycan extracted from sea cucumber, Chin J Hematol, Sep. 2006, vol. 27, No. 9, pp. 579-583, the abstract and discussion.
Wang, Xuefeng, et al., "Study on antithrombotic mechanism of glycosaminoglycan extracted from sea cucumber", Chin J New Drugs Clin Rem, Dec. 2002, vol. 21, No. 12, pp. 718-721, the abstract and discussion.

* cited by examiner

| Serial number | Retention time | Name | Peak area % | Peak area | Number of theoretical plates |
|---|---|---|---|---|---|
| 1 | 16.970 | | 100 | 345930 | 519 |
| Total | | | 100 | 345930 | |

APPLICATION OF DEPOLYMERIZED HOLOTHURIAN GLYCOSAMINOGLYCANS (DHG) IN PREPARATION OF DRUG FOR PREVENTION AND TREATMENT OF THROMBOEMBOLIC DISEASES

CROSS-REFERENCE TO RELATED APPLICATIONS

The present application is a national phase entry under 35 U.S.C. §371 of International Application No. PCT/CN2013/000217, filed Mar. 1, 2013, which claims priority from Chinese Patent Application No. 201210055824.X, filed Mar. 5, 2012, and Chinese Patent Application No. 201210306680.0, filed Aug. 24, 2012, all of which are hereby incorporated herein by reference.

TECHNICAL FIELD

The present invention relates to medical application of depolymerized holothurian glycosaminoglycans (DHG), in particular relates to application of depolymerized holothurian glycosaminoglycans with weight-average molecular weights between 26,000 Da and 45,000 Da in preparation of a drug for prevention and treatment of thromboembolic diseases, including atherosclerotic thrombotic diseases and venous thromboembolic diseases, and application of a drug for the prevention and treatment of postoperative thrombosis.

BACKGROUND ART

In the middle-aged and elderly population, the blood viscosity often gradually increases, and the possibility that thrombi are formed in platelet accumulation zones (such as coronary artery and cerebral artery) increases; accordingly, the thromboembolic diseases have become common diseases that seriously threaten the health of human beings especially the middle-aged and elderly people. Thrombosis is the main cause of arterial diseases such as myocardial infarction and stroke and venous thromboembolic diseases and patient death. The thrombosis prevention drug can be divided into anticoagulant drugs, antiplatelet drugs and direct thrombolytic drugs, etc. according to the mechanism of action, and can be clinically applied in prevention and treatment of thrombosis. The anticoagulant drugs prevent the thrombus formation or recurrence by affecting coagulation factors. The anticoagulant drugs have no dissolution function on the formed thrombi but can prevent thrombus expansion and new thrombosis. There are many kinds of existing anticoagulant drugs, but most of the anticoagulant drugs are Western medicine anticoagulant drugs with greater side effects, and the condition of blood coagulation needs to be repeatedly detected when the anticoagulant drugs are used in order to avoid bleeding. In addition, the administration mode is complex, more importantly, such anticoagulant drugs have potential risks. For example, in the use process of the currently widely used anticoagulant drugs such as heparin, low molecular weight heparin and warfarin, the condition of blood coagulation needs to be repeatedly detected, because excessive use or use to different physical persons is prone to a variety of bleedings, and there is a serious safety risk.

Therefore, it is an inevitable trend for prevention and treatment of thromboembolic diseases to screen and separate a more effective and safe drug for prevention and treatment of thromboembolic diseases from traditional Chinese medicines in consideration of the aging of the population and the increased incidence of cardiovascular diseases as well as the extensiveness of the anticoagulant drugs in clinic application to the prevention and treatment of thromboembolic diseases and the seriousness of the safety hazard of the anticoagulant drugs.

SUMMARY OF THE INVENTION

An object of the present invention is to provide an application of depolymerized holothurian glycosaminoglycanin preparation of a drug for prevention and treatment of thromboembolic diseases in order to overcome the defects of the prior art and meet the clinic requirements.

The animal experiments show that more than one type of depolymerized holothurian glycosaminoglycans with weight-average molecular weights of between 26,000 Da and 45,000 Da can be used for the prevention of atherosclerotic thrombotic diseases, for the treatment of atherosclerotic thrombotic diseases, for venous thromboembolic diseases, for the treatment of venous thromboembolic diseases, and for the prevention of postoperative thrombosis or treatment of postoperative thrombosis;

Therefore, more than one type of depolymerized holothurian glycosaminoglycans with weight-average molecular weights of between 26,000 Da and 45,000 Da can be used for preparing a drug for the prevention of atherosclerotic thrombotic diseases and venous thromboembolic diseases, for preparing a drug for the treatment of atherosclerotic thrombotic diseases and venous thromboembolic diseases, for preparing a drug for the prevention of postoperative thrombosis, or for preparing a drug for the treatment of postoperative thrombosis.

The drug comprises more than one type of depolymerized holothurian glycosaminolycans with weight-average molecular weights between 26,000 Da and 45,000 Da and a pharmaceutically acceptable carrier, and is an injection or freeze-dried powder for intravenous or subcutaneous administration;

In the drug, the weight content of depolymerized holothurian glycosaminoglycan is 90% to 99.90%, preferably 92% or more, more preferably 95% or more in order to achieve better results;

The polydispersity of depolymerized holothurian glycosaminoglycan is 1 to 2, preferably 1 to 1.5, more preferably 1 to 1.4;

The polydispersity refers to an index that measures the molecular weight distribution of polymers commonly used in the field, and is used for characterizing the width of molecular weight distribution of polymers. The polydispersity is also called a polydispersity index, polydispersity or a distribution width index in this article or other literatures, and is a ratio of weight average molecular weight (Mw) to number average molecular weight (Mn), i.e. Mw/Mn. This ratio varies with the width of the molecular weight distribution. In single-dispersion, $M_w$/Mn is equal to 1, and the Mw/Mn value gradually increases as the molecular weight distribution widens.

The subcutaneous injection dosage for rats is 10 mg/kg to 70 mg/kg, preferably 20 mg/kg to 50 mg/kg;

The intravenous injection dosage for rats is 0.5 mg/kg to 20 mg/kg, preferably 0.8 mg/kg to 15 mg/kg;

The pharmaceutically acceptable carrier is more than one selected from the group consisting of mannitol, lactose, dextran, glucose, glycine, hydrolyzed gelatin, povidone and sodium chloride, preferably mannitol;

The depolymerized holothurian glycosaminoglycans with weight-average molecular weights of between 26,000 Da and 45,000 Da can be commercially produced, e.g., the depolymerized holothurian glycosaminoglycans produced by Harbin Hongdoushan Bio-Pharm Co., Ltd., or can be produced by a method reported in Chinese Patent ZL200910305363.5, or can be prepared by the following method:

(1) an enzyme is added to minced holothurian, and then is subjected to enzymatic hydrolysis and precipitation, and then a crude product of depolymerized holothurian glycosaminoglycans is collected; the crude produced of depolymerized holothurian glycosaminoglycans is purified and decolorized to collect the depolymerized holothurian glycosaminoglycans;

The holothurian is more than one selected from the group consisting of holothuria leucospilota, holothuria atra, holothuria scabra, thelenota ananas, mensamaria intarcedens or actinopyga mauritian, preferably holothuria leucospilota;

The enzyme comprises a proteolytic enzyme and a compound pancreatin. The proteolytic enzyme can be a commercially available product, e.g., Alcalase produced by Novozymes (Shenyang) Biotechnology Co., and the compound pancreatin can be commercially produced, e.g., Xuemei compound pancreatin produced by Wuxi Xuemei Science and Technology Co., Ltd. The proteolytic enzyme accounts for 2% of holothurian by weight, and the compound pancreatin accounts for 2% of holothurian by weight;

(2) A product in a step (1) is added with hydrogen peroxide with weight concentration of 5% to 10% to be degraded to collect the depolymerized holothurian glycosaminoglycans with weight-average molecular weights of between 26,000 Da and 45,000 Da;

The preparation method of the drug is a conventional method in the preparation field, such as a method recorded in the traditional Chinese medicine preparation manual, so that the injection or freeze-dried powder is obtained;

The depolymerized holothurian glycosaminoglycans containing drug provided by the present invention can be applied to a patient to be treated by a subcutaneous or intravenous injection method, and the dosage is determined by a physician according to the patient's specific circumstances (such as age, weight, gender, disease duration, physical condition, etc.). Generally speaking, on the basis of depolymerized holothurian glycosaminoglycans, the subcutaneous injection dosage is 5 to 70 mg/kg, preferably 10 to 50 mg/kg, and the intravenous injection dosage is 0.5 to 20 mg / kg, preferably 0.8 to 15 mg/kg.

A large number of experimental studies have shown that the anticoagulant activity of depolymerized holothurian glycosaminoglycans is significantly characterized in that as the dosage increases, the increase in anticoagulant activity reduces to reduce bleeding; therefore, the anticoagulant activity of the depolymerized holothurian glycosaminoglycans has obviously excellent safety compared with heparin and low molecular weight heparin. The depolymerized holothurian glycosaminoglycans can be more safely used for the prevention and treatment of thromboembolic disease, including atherosclerotic thrombotic diseases and venous thromboembolic diseases (such as myocardial infarction, thrombophlebitis, pulmonary embolism, etc.), and can be used for the prevention and treatment of postoperative thromboembolism.

The large number of experimental studies have shown that when the drug using the depolymerized holothurian glycosaminoglycans with weight-average molecular weights of between 26,000 Da and 45,000 Da as an active ingredient is subcutaneously injected, the drug can be safely and effectively used for the prevention and treatment of thromboembolic diseases because the drug has significant anticoagulant effect and has no or has weaker bleeding or thrombocytopenia side effects, etc. The drug containing the depolymerized holothurian glycosaminoglycans with weight-average molecular weights between 26,000 Da and 45,000 Da has more excellent subcutaneous injection anticoagulant effect than depolymerized holothurian glycosaminoglycans with a weight-average molecular weight of less than 10,000 Da. For an injection of depolymerized holothurian glycosaminoglycans with weight-average molecular weights between 26,000 Da and 45,000 Da, the blood coagulation time is prolonged and the anticoagulant effect is enhanced as the dosage increases, and the increase in anticoagulant effect reduces as the dosage increases so as to reduce bleeding, therefore, the safety of the injection is much higher than that of heparin and low molecular weight heparin. In addition, the subcutaneous administration is used and is more favorable for use in the drug, while at the same time, the convenience and safety of use in the drug are improved.

BRIEF DESCRIPTION OF THE ACCOMPANYING DRAWINGS

DETAILED DESCRIPTION OF THE EMBODIMENTS

Figure 1:
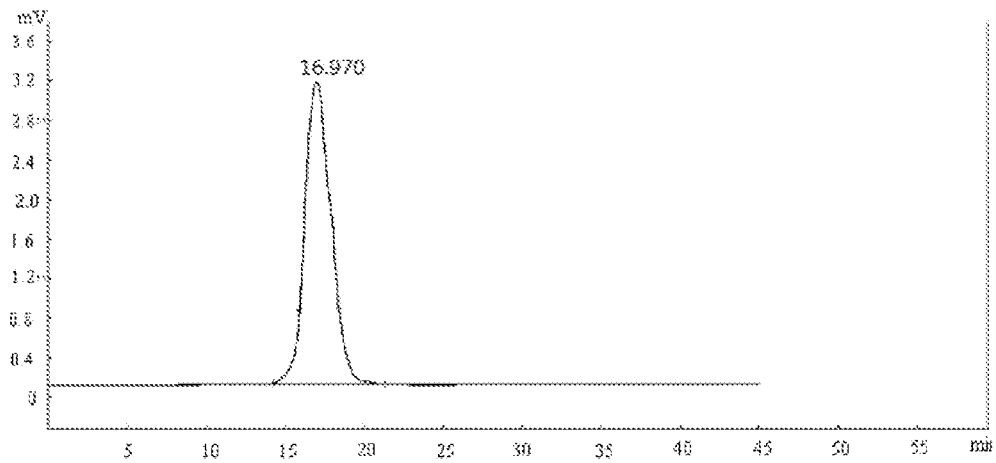
FIG. 1 shows a purity diagram of depolymerized holothurian glycosaminoglycans in a depolymerized holothurian glycosaminoglycans drug.

An extraction method of depolymerized holothurian glycosaminoglycans comprises the following steps of extracting holothuria glycosaminoglycans from holothurian, degrading and depolymerizing to obtain depolymerized holothurian glycosaminoglycans, and then collecting the depolymerized holothurian glycosaminoglycans with required molecular weights. The method for extracting the holothuria glycosaminoglycans from the body wall of holothurian is known to those skilled in the art, such as the Chinese patent ZL200910305363.5.

The weight average molecular weight is tested by a high performance liquid chromatography.

Embodiment 1

Extraction method of holothuria glycosaminoglycans comprises the following steps:

weighing 5 Kg of a crude holothuria leucospilota, and soaking in water overnight; draining the body wall of holothurian, mincing, weighing and replenishing with water to 40 Kg, placing in a 60° C. water bath, adding 6 mol/L sodium hydroxide to adjust the pH value to 8.0 ±0.2, adding 100 ml proteolytic enzyme Alcalase (Novozymes (Shenyang) Biotechnology Co.) to be stirred, and be subjected to enzymolysis for 4 hours, inactivating for 10 minutes at a temperature of 85° C. above, cooling to 50° C.±2° C., adding 6 mol/L sodium hydroxide to adjust the pH value to 8.0±0.2, adding 10 g of compound pancreatin (Wuxi Xuemei Science and Technology Co., Ltd., Xuemei brand) to be stirred and be subjected to enzymolysis for 4 hours, boiling for 10 min., and cooling; centrifuging at a temperature of 4° C. to collect a supernatant, adding 6 mol/L hydrochloric acid to adjust the pH value to 2.5±0.2, refrigerating for 2 hours at a temperature of 4° C., centrifuging to collect a supernatant, adding 6 mol/L sodium hydroxide to adjust the pH value to 7.0±0.2, adding 0.8 times ethanol, and keeping stand overnight at a temperature of 4° C.;

centrifuging, collecting a precipitate to be weighed, adding 10 times weight of distilled water, heating to 85° C.±2° C. until the precipitate is completely dissolved, adding 6 mol/L sodium hydroxide to adjust the pH value to 9.0±0.2, adding calcium chloride until the concentration of calcium chloride in a solution reaches 2% (w/v), heating to 90° C. and maintaining for 15 minutes, cooling to room temperature, centrifuging at a temperature of 4° C., collecting a supernatant, adjusting the pH value to 11.0±0.2 with a saturated sodium carbonate solution, centrifuging and collecting a supernatant, adjusting the pH value to 6.0±0.2 with 6 mol/L hydrochloric acid, adding 0.8 times volume of ethanol, and refrigerating overnight at a temperature of 4° C.;

centrifuging a refrigerated liquid and collecting a precipitate to be weighed, adding 2 times volume of distilled water, heating so that the precipitate is fully dissolved, adding potassium acetate so that the final concentration is 2 mol/L, and keeping stand overnight at a temperature 4° C.; centrifuging, collecting a precipitate to be weighed, adding 2 times volume of distilled water, heating so that the precipitate is fully dissolved, adding potassium acetate so that the final concentration is 2 mol/L, and keeping stand overnight at a temperature 4° C.; centrifuging, washing the precipitate with a 2 mol/L cold potassium acetate solution for three times, then sequentially washing with 80% ethanol, 95% ethanol, and anhydrous ethanol, drying at a temperature of 80° C. after the ethanol is fully evaporated, weighing, and obtaining a crude product A;

adding 0.05 mol/L HAc-NaAc buffer solution with a pH value of 6.0 to the crude product A of 100 g to be prepared into a 2% solution for column packing; after the solution is subjected to a cellulose chromatographic column, washing with 1.5 times column volumes of an HAc-NaAc buffer solution of 0.4 mol/LNaCl (pH6.0±0.2), and then eluting with an HAc-NaAc buffer solution of 1 mol/L NaCl (pH6.0±0.2); collecting an eluate according to the value change rate at 220 nm with an UV detector, placing in a 60° C. water bath, adjusting the pH value to 11±0.2 with NaOH, adding 3% hydrogen peroxide by volume, holding for 4 hours, cooling, centrifuging, collecting a supernatant, adjusting the pH value to 7.0±0.2 with HCl, adding 1 time ethanol, and keeping stand overnight at a temperature of 4° C.

centrifuging, collecting a precipitate, and sequentially washing with 95% ethanol and anhydrous ethanol to obtain a crude product B;

dissolving the crude product B with distilled water into a 5% solution, concentrating with a UF membrane with molecular weight cut-off of 10,000 to ½ of the original volume, replenishing water to the original volume, ultrafiltrating to ½ of the volume, adding water to repeat once, and freeze-drying an ultrafiltrate to obtain holothuria glycosaminoglycans.

1.2 Preparation Method of Depolymerized Holothurian Glycosaminoglycans

The pure holothuria glycosaminoglcan product is prepared into a 2% solution with 5% acetic acid, 30% hydrogen peroxide is added so that the concentration of hydrogen peroxide in the solution is 5%, and the controlled depolymerization is carried out for 20 hours at a temperature of 60° C. The solution is neutralized to be neutral with 0.1 mol/l sodium hydroxide, 3 times volume of ethanol is added for alcohol precipitation, and the resultant product is kept stand and centrifuged to obtain a crude product of depolymerized holothurian glycosaminoglycans.

The crude product is dried and dissolved in 5 times weight of water, is subjected to a sephadex-G75 column and is eluted with 0.5 mol/l sodium chloride to remove salts and low molecular impurities, and the desalted sample is freeze-dried to obtain 55 g of depolymerized holothurian glycosaminoglycans with molecular weight of between 26,000 Da and 45,000 Da, wherein the D value is less than 1.5, and the purity is higher than 98%.

Figure 2:
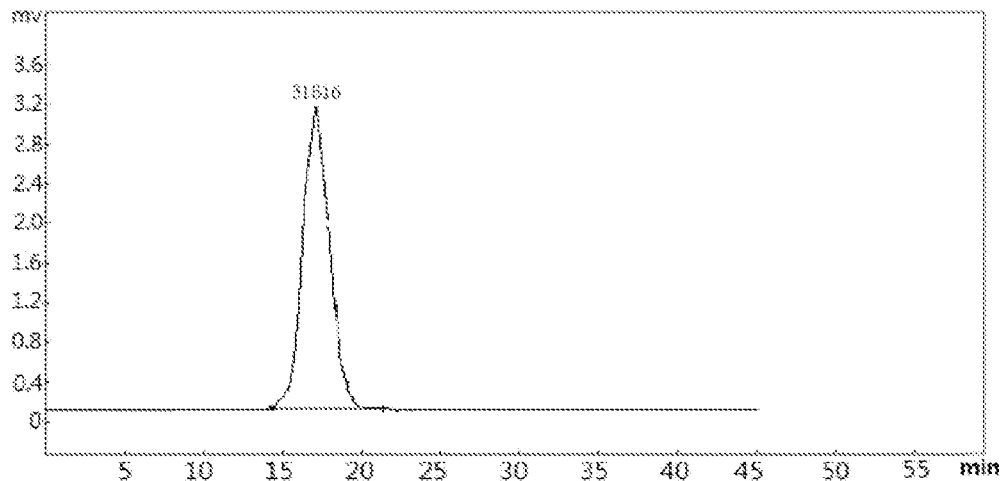
FIG. 2 shows a molecular weight distribution diagram of depolymerized holothurian glycosaminoglycans in a depolymerized holothurian glycosaminolycan drug.
Figure 3:
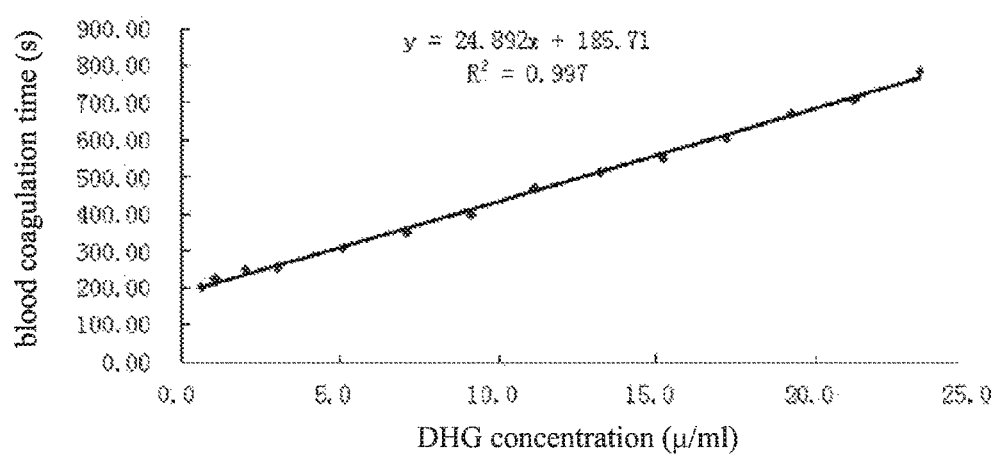
FIG. 3 is a linear relation diagram of in vitro anticoagulant dosage and blood coagulation time of DHG.

The depolymerized holothurian glycosaminoglycans obtained from the embodiment is subjected to a differential refractive index detector (RID-10A, Shimadzu) to obtain a pure product with a purity of 99.0% (Chromatogram can be seen in FIG. 1). The depolymerized holothurian glycosaminoglycans obtained from the embodiment is subjected to a gel column (TSK gel G4000PWXL, TOSOH) for chromatographic analysis, it can be known that the weight average molecular weight of the product is 31816, and the D value is 1.36 (Chromatogram can be seen in FIG. 2)

The obtained depolymerized holothurian glycosaminoglycans of 12.0 g is added with 24 g of mannitol, is added with 1000 ml water for injection to be dissolved, and is ultrafiltrated, packed and freeze-dried to obtain 1000 bottles of depolymerized holothurian glycosaminoglycans freeze-drying powder for injection.

Embodiment 2

Pharmacodynamic experiments of depolymerized holothurian glycosaminoglycans 2.1 In vitro Anticoagulant Experiment 2.1.1 Test Materials Test Samples:

Name: depolymerized holothurian glycosaminoglycans (26,000 Da to 45,000 Da), DHG for short;

Source: Shanghai Kairun Bio-Medical Co., Ltd.

Batch number: 20110308;

Preparation: after precise suction, the normal saline for injection is used for diluting to the desired concentration.

Test Animals

Strain: rabbit;

Source: Shanghai Chenhang experimental rabbit Co. Ltd.;

Gender: male;

Weight: 1800 g;

Animal Certificate Number: SCXK (Shanghai) 2007-0010.

2.1.2 Test Instrument

Platelet aggregation and coagulation factor analyzer (Model: LG-PABER Beijing Steellex Scientific Instrument Company).

2.1.3 Experimental Method

On the experimental day, 80 µl of rabbit plasma and 10 µl of a 0.9% sodium chloride solution are respectively added to sample pools, and are preheated for 180 s, and then 10 µl of a 1% calcium chloride solution is added to be evenly mixed at once to avoid generating air bubbles, and then the platelet aggregation and coagulation factor analyzer is used to start calculating time, and the coagulation time of each sample pool is recorded, i.e., a blank group.

A control solution is precisely weighed, is diluted with a 0.9% sodium chloride solution to solutions of different concentrations, i.e., sample solutions of different concentrations (0.6 µg/ml to 23.3 µg/ml).

10 µl of sample solutions of different concentrations replace 10 µl of a 0.9% sodium chloride solution to respectively determine the plasma coagulation time of the sample solution of each concentration. The parallel determination is carried out for 4 times for each concentration, and an average value is given.

2.1.4 Experimental Results

Experimental results show that the final concentration of the sample is in a dosage range of 0.6 µg/ml to 23.3 µg/ml, the blood coagulation time is prolonged as the dosage increases, and the increasing trend eases as the blood coagulation time is prolonged. Therefore, the DHG composition has better safety and controllability in anticoagulation.

TABLE 1

In vitro anticoagulant experimental results of DHG

| Samples (µg/ml) | Blood coagulation time | Samples (µg/ml) |
|---|---|---|
| Blank | 197.2 ± 10.5 | |
| 0.6 | 198.3 ± 13.8 | 0.6% |
| 1.0 | 226.7 ± 12.7 | 15.0% |
| 2.0 | 248.3 ± 6.2 | 26.0% |
| 3.0 | 253.9 ± 8.2 | 28.8% |
| 5.1 | 309.8 ± 25.6 | 57.1% |
| 7.1 | 351.5 ± 21.5 | 78.3% |
| 9.1 | 401.5 ± 23.2 | 103.7% |
| 11.1 | 471.4 ± 20.6 | 139.1% |
| 13.2 | 512.7 ± 9.5 | 160.1% |
| 15.2 | 551.4 ± 17.1 | 179.7% |
| 17.2 | 603.6 ± 35.8 | 206.1% |
| 19.2 | 669.7 ± 12.6 | 239.7% |
| 21.3 | 709.6 ± 23.4 | 259.9% |
| 23.3 | 784.8 ± 37.6 | 298.0% |

2.2 Effect of Subcutaneously Injected DHG on Rate Blood Coagulation System 2.2.1 Test Materials Test Samples:

Name: DHG;

Source: Shanghai Kairun Bio-Medical Co., Ltd.

Batch Number: 20110308;

Preparation: after precise suction, the normal saline for injection is used for diluting to the desired concentration.

2.2.2 Test Animals

Strains: SD rats;

Source: Shanghai Super—B&K experimental animal Co, Ltd.

Gender: male;

Weight: 220-250 g;

Animal Certificate Number: SCXK (Shanghai) 2011-0017;

Breeding: Animals are bred in purifying positive pressure ventilation animal rooms at a room temperature of 23±1° C., and a humidity of 50 to 70%, the artificial lighting simulates diurnal variation, and the animals freely eat food and drink water.

2. 2.3 Test Instrument

Automatic Coagulation Analyzer Sysmex CA-1500

2.2.4 Experimental Method

40 SD rats are divided into four different administration groups, i.e., a negative control group (subcutaneously injected with 0.5 ml of normal saline), low, middle and high-dose (10, 20 and 40 mg/kg) depolymerized holothurian glycosaminolycan (26,0000 Da to 45,0000 Da) (DHG) groups, and the rats are administered by subcutaneous injection by the volume of 0.5 ml.

At 60 minutes after the low, middle and high-dose DHG groups and the blank control group are administrated by subcutaneous injection, the values of the prothrombin time (PT), the activated partial thromboplastin time (APTT) and the thrombin time (TT) are determined by collecting blood from the abdominal aorta. See Table 2.

At 10 minutes before a surgery, the animals in each group are intraperitoneally injected with 3% Seconal to be anesthetized (0.1 ml/100 g body weight), and are supinely fixed to undergo an abdominal surgery, and the blood is collected by a disposable 3.2% sodium citrate anticoagulant vacuum blood collection tube.

2.2.5 Test Results

The effects of DHG at a low dose of 10 mg/kg on APTT, TT and PT are obvious, i.e., APTT, TT and PT are prolonged by 190.8%, 90.3% and 10.4% respectively, and the effects of DHG at doses of 20 mg/kg and 40 mg/kg on APTT, TT and PT are extremely significant, i.e., APTT exceeds a range of between 150% and 250%. See Table 3.

TABLE 2

Experimental results of anticoagulation of rats subcutaneously injected with DHG

| | | Blood coagulation time (mean ± SD) | | |
|---|---|---|---|---|
| Groups | Animal number | PT (sec) | APTT (sec) | TT (sec) |
| 10 mg/kg | 10 | 9.5 ± 0.2 | 34.7 ± 1.5 | 98.3 ± 7.1 |
| 20 mg/kg | 10 | 10.0 ± 0.3 | 54.4 ± 3.4 | 112.0 ± 8.8 |
| 40 mg/kg | 10 | 11.1 ± 0.9 | 63.4 ± 5.3 | 130.4 ± 9.4 |
| Blank | 10 | 8.6 ± 0.2 | 11.9 ± 1.3 | 51.6 ± 3.8 |

TABLE 3

Blood coagulation time prolonging rate of DHG rats

| | PT | APTT | TT |
|---|---|---|---|
| 10 mg/kg | 10.4% | 190.8% | 90.3% |
| 20 mg/kg | 15.1% | 355.2% | 116.8% |
| 40 mg/kg | 28.3% | 430.5% | 152.5% |

2.3 Effect of Depolymerized Holothurian Glycosaminolycan on Rat Arteriovenous Catheter Thrombosis Model 2.3.1 Test Materials Test Samples Name: DHG Source: Shanghai Kairun Bio-Medical Co., Ltd.

Batch number: 20110306;

Preparation: after precise suction, the normal saline for injection is used for diluting to the desired concentration.

Control Sample:

Name: Heparin;

Source: Sinopharm Chemical Reagent Co., Ltd.;

Batch number: F20091029;

Content: 150 U/mg;

Preparation: after precise suction, the normal saline for injection is used for dissolving and diluting to the desired concentration.

Test Animals:

Strains: SD rats;

Source: Shanghai Super—B&K experimental animal Co, Ltd.

Gender: male; Weight: 250-300 g;

Animal Certificate Number: SCXK (Shanghai) 2011-0007;

Breeding: Animals are bred in purifying positive pressure ventilation animal rooms at a room temperature of 23±1° C., and a humidity of 50 to 70%, the artificial lighting simulates diurnal variation, and the animals freely eat food and drink water.

2.3.2 Test Instrument

BS 110 s-type electronic balance, produced by SARTORIUS Company, with the minimum weight of 0.1 mg.

2.3.3 Test Method

34 SD rats are divided into four different administration groups, i.e., a negative control group (normal saline 1 ml/kg), two DHG dose groups (10, 20 mg/kg), and a positive control low molecular weight heparin group (2 mg/kg). All drugs are subcutaneously injected for administration by the volume of 0.5 ml.

The animals in each group are intraperitoneally injected with 12% chloral hydrate to be anesthetized (350 to 400 mg/kg) at 10 min before a surgery, and then are supinely fixed. The neck skin is cut off, and the left carotid artery and the right external jugular vein are dissected to be connected by a bypass pipe in which a 7 cm long No. 4 surgical silk thread is placed. The bloodstream is opened for 15 minutes at 20 minutes after administration respectively, and then the silk thread is taken out to be weighed, and the weight of the silk thread is deducted to obtain the thrombus wet weight. The thrombus wet weight mean and standard deviation of each test group are calculated and are compared with those of the normal saline group by a t-test. The thrombus wet weight inhibition rate of each test group is calculated in accordance with the following formula:

Thrombus wet weight inhibition rate (%)=(Thrombus wet weight (solvent group)−Thrombus wet weight (test group)/Thrombus wet weight (solvent group))*100%

2.3.4 Test Results

See Table 4, at 20 minutes after administration, the positive drug and the test drug can obviously inhibit thrombus formation after being tested. The inhibition of the test drug on thrombus formation is proportional to the dosage.

TABLE 4

Effect of DHG on rat arteriovenous catheter thrombosis model

| Group | n | Dosage (mg/kg) | Thrombus weight (mg) 20 minutes | Thrombus inhibition rate (%) 20 minutes |
|---|---|---|---|---|
| Blank | 10 | 0.5 ml | 66.9 ± 4.2 | |
| LMWH | 8 | 2 | 40.8 ± 3.8** | 39.0% |
| DHG | 8 | 10 | 49.2 ± 5.1* | 26.5% |
| | 8 | 20 | 30.2 ± 6.8** | 54.9% |

Compared with the negative group:
*P < 0.05,
**P < 0.01

2.4 Effect of Subcutaneously Injected DHG with Different Molecular Weight Segments on Rat Blood Coagulation System 2.4.1 Test Materials Test Samples:

Name: DHG-I (8000 Da to 12000 Da); DHG-II (26,000 Da to 45,000 Da); [0127] Source: Shanghai Kairun Bio-Medical Co., Ltd.

Batch numbers: 20110309 (DHG-I); 20110308 (DHG-II);

Preparation: after precise suction, the normal saline for injection is used for diluting to the desired concentration.

2.4.2 Test Animals

Strain: SD rats;

Source: Shanghai Super—B&K experimental animal Co, Ltd.

Gender: male;

Weight: 220-250 g;

Animal Certificate Number: SCXK (Shanghai) 2011-0017;

Breeding: Animals are bred in purifying positive pressure ventilation animal rooms at a room temperature of 23±1° C., and a humidity of 50 to 70%, the artificial lighting simulates diurnal variation, and the animals freely eat food and drink water.

2.4.3 Test Instrument

Automatic Coagulation Analyzer Sysmex CA-1500

2.4.4 Experimental Method

40 SD rats are divided into four different administration groups, i.e., a negative control group (subcutaneously injected with normal saline of 0.5 ml), DHG with different molecular weight segments, DHG-I (8,000 Da to 12,000 Da), DHG-II (26,000 Da to 45,000 Da); the rats are subcutaneously injected at the same dose of 20 mg/kg by the volume of 0.5 ml.

At 60 minutes after the DHG with different molecular weight segments and the blank control group are administrated by subcutaneous injection, the values of the prothrombin time (PT), the activated partial thromboplastin time (APTT) and the thrombin time (TT) are determined by collecting blood from the abdominal aorta. See Table 5. At 10 minutes before a surgery, the animals in each group are intraperitoneally injected with 3% Seconal to be anesthetized (0.1 ml/100 g body weight), and are supinely fixed to undergo the abdominal surgery, and the blood is collected by a disposable 3.2% sodium citrate anticoagulant vacuum blood collection tube.

2.4.5 Test Results

The effect of DHG-II on APTT, TT and PT is obviously stronger than that of DHG-I at the same does. For DHG-I, the APTT, TT and PT are respectively prolonged by 157.3%, 51.4% and 37.0%. For DHG-II, the APTT, TT and PT are respectively prolonged by 365.0%, 117.9% and 37.0%. See Table 6.

TABLE 5

Experimental results of anti-coagulation of rats subcutaneously injected with DHG with different molecular weight segments

| Groups | Animal number | Blood coagulation time (mean ± SD) | | |
|---|---|---|---|---|
| | | PT (sec) | APTT (sec) | TT (sec) |
| DHG-I | 10 | 8.0 ± 0.3 | 30.1 ± 1.4 | 77.8 ± 6.9 |
| DHG-II | 10 | 10.0 ± 0.3 | 54.4 ± 3.4 | 112.0 ± 8.8 |
| Blank | 10 | 7.3 ± 0.4 | 11.7 ± 1.2 | 51.4 ± 5.2 |

TABLE 6

Blood coagulation time prolonging rate of rats injected with DHG with different molecular weight segments

| | PT | APTT | TT |
|---|---|---|---|
| 20 mg/kg | 9.6% | 157.3% | 51.4% |
| 20 mg/kg | 37.0% | 365.0% | 117.9% |

2.5 Effect of Intravenously Injected DHG on Rat Blood Coagulation System 2.5.1 Test Materials Test Samples:

Name: DHG

Source: Shanghai Kairun Bio-Medical Co., Ltd.

Batch number: 20110308;

Preparation: after precise suction, the normal saline for injection is used for diluting to the desired concentration.

2.5.2 Test Animals

Strain: SD rats;

Source: Shanghai Super—B&K experimental animal Co, Ltd.

Gender: male;

Weight: 220-250 g;

Animal Certificate Number: SCXK (Shanghai) 2011-0017;

Breeding: Animals are bred in purifying positive pressure ventilation animal rooms at a room temperature of 23±1° C., and a humidity of 50 to 70%, the artificial lighting simulates diurnal variation, and the animals freely eat food and drink water.

2.5.3 Test Instrument

Automatic Coagulation Analyzer Sysmex CA-1500

2.2.4 Experimental Method

40 SD rats are divided into four different administration groups, i.e., a negative control group (intravenously injected with 0.2 ml of normal saline), low, middle and high-dose depolymerized holothurian glycosaminolycan (26,0000 Da to 45,0000 Da) (DHG) groups (0.5, 1.5 and 4.5 mg/kg), and the rats are administered by subcutaneous injection by the volume of 0.2 ml.

At 30 minutes after the low, middle and high-dose DHG groups and the blank control group are administrated by subcutaneous injection, the values of the prothrombin time (PT), the activated partial thromboplastin time (APTT) and the thrombin time (TT) are determined by collecting blood from the abdominal aorta. See Table 7.

At 10 minutes before a surgery, the animals in each group are intraperitoneally injected with 3% Seconal to be anesthetized (0.1 ml/100 g body weight), and are supinely fixed to undergo the abdominal surgery, and the blood is collected by a disposable 3.2% sodium citrate anticoagulant vacuum blood collection tube.

2.2.5 Test Results

The effects of DHG at a low dose of 0.5 mg/kg on APTT, TT and PT are significant, i.e., APTT, TT and PT are prolonged by 157.27%, 83.80% and 2.35% respectively, and the effects of DHG at doses of 1.5 mg/kg and 4.5 mg/kg on APTT, TT and PT are extremely obvious, i.e., APTT exceeds a range of between 150% and 200%. See Table 8.

TABLE 7

Experimental results of anti-coagulation of rats intravenously injected with DHG

| Groups | Animal number | PT (sec) | APTT(sec) | TT (sec) |
|---|---|---|---|---|
| | | | Blood coagulation time (mean ± SD) | |
| 0.5 mg/kg | 10 | 8.7 ± 0.3 | 28.3 ± 1.3 | 85.1 ± 6.2 |
| 1.5 mg/kg | 10 | 9.4 ± 0.5 | 34.4 ± 2.8 | 102.1 ± 7.6 |
| 4.5 mg/kg | 10 | 10.8 ± 0.7 | 53.4 ± 4.7 | 122.4 ± 8.1 |
| Blank | 10 | 8.5 ± 0.3 | 11.0 ± 1.1 | 46.3 ± 3.7 |

TABLE 3

Blood coagulation time prolonging rate of DHG rats

| | PT | APTT | TT |
|---|---|---|---|
| 0.5 mg/kg | 2.35% | 157.27% | 83.80% |
| 1.5 mg/kg | 10.59% | 212.73% | 120.52% |
| 4.5 mg/kg | 27.06% | 385.45% | 164.36% |

What is claimed is:

1. A depolymerized holothurian glycosaminoglycan (DHG) that is used for the preparation of a drug for prevention or treatment of thromboembolic diseases, wherein the drug comprises a depolymerized holothurian glycosaminoglycan and a pharmaceutically acceptable carrier, wherein the depolymerized holothurian glycosaminoglycan has a weight-average molecular weight within the range of from about 26,000 Da and 45,000 Da, wherein the depolymerized holothurian glycosaminoglycan is prepared via a process that comprises the steps as follows:

(1) mincing a holothurian, wherein the holothurian is Holothuria leucospilota, (2) adding an enzyme into the minced holothurian, wherein the enzyme comprises a proteolytic enzyme and a compound pancreatin, an amount of the proteolytic enzyme is 2% of a weight of the holothurian, and an amount of the compound pancreatin is 2% of the weight of the holothurian;

(3) performing an enzymatic hydrolysis and precipitation on the product of step (2) to form a holothurian glycosaminoglycan, (4) collecting a crude product of holothurian glycosaminoglycan, (5) purifying and decolorizing the crude product of holothurian glycosaminoglycan, and (6) collecting the holothurian glycosaminoglycan;

(7) adding hydrogen peroxide with a weight concentration of about 5% to about 10% into a product obtained in the step (6) for degradation, (8) collecting a depolymerized holothurian glycosaminoglycan with a weight average molecular weight within a range of from 26,000 Da to 45,000 Da.

2. A depolymerized holothurian glycosaminoglycan (DHG) that is used for the preparation of a drug for prevention or treatment peripheral vascular thrombosis obliterans diseases, wherein the drug comprises depolymerized holothurian glycosaminoglycan and a pharmaceutically acceptable carrier, in which the depolymerized holothurian glycosaminoglycan has a weight-average molecular weights between 26,000 Da and 45,000 Da;

wherein the depolymerized holothurian glycosaminoglycan is prepared via a process that comprises the steps as follows:

(1) mincing a holothurian, wherein the holothurian is Holothuria leucospilota, (2) adding an enzyme into the minced holothurian, wherein the enzyme comprises a proteolytic enzyme and a compound pancreatin, an amount of the proteolytic enzyme is 2% of a weight of the holothurian, and an amount of the compound pancreatin is 2% of the weight of the holothurian;

(3) performing an enzymatic hydrolysis and precipitation on the product of step (2) to form a holothurian glycosaminoglycan, (4) collecting a crude product of holothurian glycosaminoglycan, (5) purifying and decolorizing the crude product of holothurian glycosaminoglycan, and (6) collecting the holothurian glycosaminoglycan;

(7) adding hydrogen peroxide with a weight concentration of about 5% to about 10% into a product obtained in the step (6) for degradation, (8) collecting a depolymerized holothurian glycosaminoglycan with a weight average molecular weight within a range of from 26,000 Da to 45,000 Da.

3. A depolymerized holothurian glycosaminoglycan (DHG) that is used for the preparation of a drug for prevention or treatment, wherein the drug comprises depolymerized holothurian glycosaminoglycan and a pharmaceutically acceptable carrier, in which the depolymerized holothurian glycosaminoglycan has a weight-average molecular weights between 26,000 Da and 45,000 Da;
   wherein the depolymerized holothurian glycosaminoglycan is prepared via a process that comprises the steps as follows:
   (1) mincing a holothurian, wherein the holothurian is Holothuria leucospilota,
   (2) adding an enzyme into the minced holothurian, wherein the enzyme comprises a proteolytic enzyme and a compound pancreatin, an amount of the proteolytic enzyme is 2% of a weight of the holothurian, and an amount of the compound pancreatin is 2% of the weight of the holothurian;
   (3) performing an enzymatic hydrolysis and precipitation on the product of step (2) to form a holothurian glycosaminoglycan,
   (4) collecting a crude product of holothurian glycosaminoglycan,
   (5) purifying and decolorizing the crude product of holothurian glycosaminoglycan, and
   (6) collecting the holothurian glycosaminoglycan;
   (7) adding hydrogen peroxide with a weight concentration of about 5% to about 10% into a product obtained in the step (6) for degradation,
   (8) collecting a depolymerized holothurian glycosaminoglycan with a weight average molecular weight within a range of from 26,000 Da to 45,000 Da.

4. The depolymerized holothurian glycosaminoglycan as set forth in claim 1, which is characterized in that the depolymerized holothurian glycosaminoglycan has a polydispersity of between 1 and 2, wherein the DHG comprises at least a first depolymerized holothurian glycosaminoglycan having a weight-average molecular weight within the range of from about 26,000 Da and 45,000 Da and a second depolymerized holothurian glycosaminoglycan having a weight-average molecular weight within the range of from about 26,000 Da and 45,000 Da, wherein the first depolymerized holothurian glycosaminoglycan and second depolymerized holothurian glycosaminoglycan are different.

5. The depolymerized holothurian glycosaminoglycan as set forth in claim 1, which is characterized in that the drug is an injection or a freeze-dried powder for intravenous or subcutaneous administration.

6. The depolymerized holothurian glycosaminoglycan as set forth in claim 4, which is characterized in that the pharmaceutically acceptable carrier is more than one selected from the group consisting of mannitol, lactose, dextran, glucose, glycine, hydrolyzed gelatin, povidone and sodium chloride.

7. The depolymerized holothurian glycosaminoglycan as set forth in claim 5, which is characterized in that the pharmaceutically acceptable carrier is more than one selected from the group consisting of mannitol, lactose, dextran, glucose, glycine, hydrolyzed gelatin, povidone and sodium chloride.

8. A depolymerized holothurian glycosaminoglycan (DHG) that is used for the preparation of a drug for prevention or treatment of cardiovascular diseases or peripheral vascular thrombosis obliterans diseases, which is characterized in that the drug comprises more than one of depolymerized holothurian glycosaminoglycans with weight-average molecular weights between 26,000 Da and 45,000 Da and a pharmaceutically acceptable carrier;
   (1) mincing a holothurian, wherein the holothurian is Holothuria leucospilota,
   (2) adding an enzyme into the minced holothurian, wherein the enzyme comprises a proteolytic enzyme and a compound pancreatin, an amount of the proteolytic enzyme is 2% of a weight of the holothurian, and an amount of the compound pancreatin is 2% of the weight of the holothurian;
   (3) performing an enzymatic hydrolysis and precipitation on the product of step (2) to form a holothurian glycosaminoglycan,
   (4) collecting a crude product of holothurian glycosaminoglycan,
   (5) purifying and decolorizing the crude product of holothurian glycosaminoglycan, and
   (6) collecting the holothurian glycosaminoglycan;
   (7) adding hydrogen peroxide with a weight concentration of about 5% to about 10% into a product obtained in the step (6) for degradation,
   (8) collecting a depolymerized holothurian glycosaminoglycan with a weight average molecular weight within a range of from 26,000 Da to 45,000 Da.

9. A depolymerized holothurian glycosaminoglycan (DHG) that is used for the preparation of a drug for prevention or treatment of postoperative thrombotic diseases, which is characterized in that the drug comprises more than one of depolymerized holothurian glycosaminoglycan with weight-average molecular weights between 26,000 Da and 45,000 Da and a pharmaceutically acceptable carrier;
   (1) mincing a holothurian, wherein the holothurian is Holothuria leucospilota,
   (2) adding an enzyme into the minced holothurian, wherein the enzyme comprises a proteolytic enzyme and a compound pancreatin, an amount of the proteolytic enzyme is 2% of a weight of the holothurian, and an amount of the compound pancreatin is 2% of the weight of the holothurian;
   (3) performing an enzymatic hydrolysis and precipitation on the product of step (2) to form a holothurian glycosaminoglycan,
   (4) collecting a crude product of holothurian glycosaminoglycan,
   (5) purifying and decolorizing the crude product of holothurian glycosaminoglycan, and
   (6) collecting the holothurian glycosaminoglycan;
   (7) adding hydrogen peroxide with a weight concentration of about 5% to about 10% into a product obtained in the step (6) for degradation,
   (8) collecting a depolymerized holothurian glycosaminoglycan with a weight average molecular weight within a range of from 26,000 Da to 45,000 Da.

10. The drug as set forth in claim 8, which is applied to a patient by intravenous or subcutaneous injection.

11. The depolymerized holothurian glycosaminoglycan as set forth in claim 2, which is characterized in that the depolymerized holothurian glycosaminoglycan has a polydispersity of between 1 and 2, and the weight average molecular weight is a plurality of different values widely distributed within the range of from 26,000 Da to 45,000 Da.

12. The depolymerized holothurian glycosaminoglycan as set forth in claim 3, which is characterized in that the depolymerized holothurian glycosaminoglycan has a polydispersity of between 1 and 2, and the weight average molecular weight is a plurality of different values widely distributed within the range of from 26,000 Da to 45,000 Da.

13. The depolymerized holothurian glycosaminoglycan as set forth in claim 2, which is characterized in that the drug is an injection or a freeze-dried powder for intravenous or subcutaneous administration.

14. The depolymerized holothurian glycosaminoglycan as set forth in claim 3, which is characterized in that the drug is an injection or a freeze-dried powder for intravenous or subcutaneous administration.

15. The depolymerized holothurian glycosaminoglycan as set forth in claim 11, which is characterized in that the pharmaceutically acceptable carrier is more than one selected from the group consisting of mannitol, lactose, dextran, glucose, glycine, hydrolyzed gelatin, povidone and sodium chloride.

16. The depolymerized holothurian glycosaminoglycan as set forth in claim 12, which is characterized in that the pharmaceutically acceptable carrier is more than one selected from the group consisting of mannitol, lactose, dextran, glucose, glycine, hydrolyzed gelatin, povidone and sodium chloride.

17. The depolymerized holothurian glycosaminoglycan as set forth in claim 13, which is characterized in that the pharmaceutically acceptable carrier is more than one selected from the group consisting of mannitol, lactose, dextran, glucose, glycine, hydrolyzed gelatin, povidone and sodium chloride.

18. The depolymerized holothurian glycosaminoglycan as set forth in claim 14, which is characterized in that the pharmaceutically acceptable carrier is more than one selected from the group consisting of mannitol, lactose, dextran, glucose, glycine, hydrolyzed gelatin, povidone and sodium chloride.

19. The drug as set forth in claim 9, which is applied to a patient by intravenous or subcutaneous injection.

* * * * *